US005614529A

United States Patent [19]
Wall et al.

[11] Patent Number: 5,614,529
[45] Date of Patent: Mar. 25, 1997

[54] INHIBITION OF PLASMODIA PARASITES BY CAMPTOTHECIN COMPOUNDS

[75] Inventors: Monroe E. Wall, Chapel Hill; Mansukh C. Wani, Durham, both of N.C.; Robert R. Engle, 8305 Tuckerman La., Potomac, Md. 20854; Robert E. Miller, 6742 Meadowside Dr., Frederick, Md. 21702

[73] Assignees: Research Triangle Institute, Research Triangle Park, N.C.; Robert R. Engle, Potomac; Robert E. Miller, Frederick, both of Md.

[21] Appl. No.: 309,467

[22] Filed: Sep. 22, 1994

[51] Int. Cl.⁶ .................. A61K 31/44; A61K 31/395; A61K 31/55; A01N 43/00
[52] U.S. Cl. ................ 514/279; 514/210; 514/211; 514/212; 514/218
[58] Field of Search ................................ 514/279, 210, 514/211, 212, 218

[56] References Cited

U.S. PATENT DOCUMENTS

| | | | |
|---|---|---|---|
| 4,031,098 | 6/1977 | Sugasawa | 260/287 C |
| 4,473,692 | 9/1984 | Miyasaka et al. | 546/48 |
| 4,545,880 | 10/1985 | Miyasaka et al. | 204/158 |
| 4,604,463 | 8/1986 | Miyasaka et al. | 544/125 |
| 4,894,456 | 1/1990 | Wall et al. | 546/41 |
| 4,914,205 | 4/1990 | Sawada et al. | 546/70 |
| 4,943,579 | 7/1990 | Vishnuvajjala et al. | 514/283 |
| 4,981,968 | 1/1991 | Wall et al. | 544/361 |
| 5,049,668 | 9/1991 | Wall et al. | 540/481 |
| 5,053,512 | 10/1991 | Wani et al. | 546/41 |
| 5,106,742 | 4/1992 | Wall et al. | 435/233 |
| 5,122,526 | 6/1992 | Wall et al. | 514/253 |
| 5,122,606 | 6/1992 | Wani et al. | 546/41 |
| 5,180,722 | 1/1993 | Wall et al. | 514/219 |
| 5,225,404 | 7/1993 | Giovannella et al. | 514/81 |
| 5,227,380 | 7/1993 | Wall et al. | 514/253 |
| 5,244,903 | 9/1993 | Wall et al. | 514/279 |
| 5,340,817 | 8/1994 | Wall et al. | 514/279 |

FOREIGN PATENT DOCUMENTS

| | | |
|---|---|---|
| 0074256 | 3/1983 | European Pat. Off. . |
| 0220601 | 5/1987 | European Pat. Off. . |
| 59-5188 | 1/1984 | Japan . |
| 59-51289 | 3/1984 | Japan . |
| 59-51287 | 3/1984 | Japan . |
| 61-50985 | 3/1986 | Japan . |
| 61-85389 | 4/1986 | Japan . |
| 61-85319 | 4/1986 | Japan . |

OTHER PUBLICATIONS

Chemical Abstracts, vol. 90, No. 3, AN 22857v (Citation), 1984.
Chemical Abstracts, vol. 92, No. 3, AN 18799b (Citation), 1986.
Chemical Abstracts, vol. 92, No. 5, AN 37766e (Citation), 1986.
Chemical Abstracts, vol. 94, No. 1, AN 4143n (Citation), 1988.
Chemical Abstracts, vol. 94, No. 12, AN 90169e (Citation), 1988.
Chemical Abstracts, vol. 95, No. 15, AN 133209h (Citation), 1989.
Chemical Abstracts, vol. 96, No. 9, AN 69271p (Citation), 1989.
Chemical Abstracts, vol. 100, No. 21, AN 167724j (Citation), 1990.
Chemical Abstracts, vol. 101, AN 78770z (Citation), 1991.
Chemical Abstracts, vol. 103, No. 9, AN 64374c (Citation), 1992.
T.R. Govindachari, et al., "9–Methoxycamptothecin: A New Alkaloid from Mappia Foetida Miers," pp. 453–454, 1989.
Proceedings of the Annual Meeting of the American Association for Cancer Research, 1989, AN 30:A2485, R.P. Hertzberg, et al., "Irreversible Trapping of the DNA–Topoisomerase I Covalent Complex and Affinity Labeling of the Camptothecin Binding Site with 10–Bromoacetamidomethylcamptothecin" (Abstract).
Proceedings of the Annual Meeting of the American Association for Cancer Research, 1989, AN 30:A2476, Y.H. Hsiang, et al., "Structure–Activity Studies of 20(S)–Camptothecin Analogs" (Abstract).
Proceedings of the Annual Meeting of the American Society of Clinical Oncology, 1989, AN 8:A1019, R. Ohno, et al., "A Clinical Study of a Camptothecin Derivative, CPT–11, on Hematological Malignacies" (Abstract).
Journal of Medicinal Chemistry, vol. 32, No. 3, Mar. 1989, R.P. Hertzberg, et al., "Modification of the Hydroxy Lactone Ring of Camptothecin: Inhibiton of Mammalian Topoisomerase I and Biological Activity" (Abstract).
Database WPI, Derwent Publications Ltd., AN 84–110812/18, JP–A–59 051 288, Mar. 24, 1984.
Database WPI, Derwent Publications Ltd., AN 84–104015/17, JP–A–59 046 284, Mar. 15, 1984.
Chemical Abstracts, vol. 101, 1984, An 101–130677r.
Chemical Abstracts, vol. 101, 1984, AN 101–91322z.
Chemical Abstracts, vol. 97, 1982, AN 97–188278b.
Chemical Abstracts, vol. 84, p. 786, Compound 115631h, 1980.
J. Org. Chem., vol. 39, No. 23, 1974, S. Danishefsky, et al., "Synthesis and Biological Evaluation of DE–AB–Camptothecin", pp. 3430–3432.
Molecular and Cellular Biology, vol. 7, No. 1, Jan. 1987, David S. Gilmour, et al., "Localization of Specific Topoisomerase I Interactions within the Transcribed Region of Active Heat Shock Genes by Using the Inhibitor Camptothecin", pp. 141–148.
Database WPI, Derwent Publications Ltd., AN 89–179979/25, Dec. 1, 1987, EP321 122, Jun. 21, 1989.
Chemical Abstracts, vol. 100, 1984, p. 683, AN 100–139434w.

(List continued on next page.)

*Primary Examiner*—Jerome D. Goldberg
*Attorney, Agent, or Firm*—Oblon, Spivak, McClelland, Maier & Neustadt, P.C.

[57] ABSTRACT

Camptothecin compounds are effective inhibitors of plasmodia growth and are useful in treating plasmodia infections in livestock, other domestic animals and humans.

14 Claims, No Drawings

OTHER PUBLICATIONS

Chemical Abstracts, vol. 84, 1976, p. 13, AN 84–115629p.

Acta Pharmaceutica Sinica, vol. 23, No. 3, 1988, pp. 186–188, L.Z. Lin, et al., "A New Alkaloid–18–Hydroxycamptothecin" (with English Abstract).

Journal of the American Chemical Society, vol. 94, No. 24, Nov. 29, 1972, Jacob J. Plattner, et al., "Synthesis of Some DE and CDE Ring Analogs of Camptothecin", pp. 8613–8615.

J. Org. Chem., vol. 39, No. 3, 1974, Jacob J. Plattner, et al., "Synthesis of Some DE and CDE Ring Analogs of Camptothecin", pp. 303–311.

Journal of Labelled Compounds and Radiopharmaceuticals, vol. XVIII, No. 3, Oct. 5, 1979, Peter E. Ronman, et al., "The Preparation of Tritium and Deuterium–Labelled Camptothecin", pp. 319–329.

The Journal of Biological Chemistry, vol. 260, No. 27, Nov. 25, 1985, Yaw–Huei Hsiang, et al., "Camptothecin Induces Protein–Linked DNA Breaks Via Mammalian DNA Topoisomerase I", pp. 14873–14878.

Journal of Medicinal Chemistry, vol. 33, No. 3, 1990, Allan W. Nicholas, et al., "Plant Antitumor Agents, 29. Synthesis and Biological Activity of Ring D and Ring E Modified Analogues of Camptothecin", pp. 972–978.

Journal of Medicinal Chemistry, vol. 30, No. 10, 1987, Mansukh C. Wani, et al., "Plant Antitumor Agents. 25. Total Synthesis and Antileukemic Activity of Ring A Substituted Camptothecin Analogues. Structure–Activity Correlations", pp. 1744–1779.

J. Med. Chem., vol. 29, 1986, Mansukh C. Wani, et al., "Plant Antitumor Agents. 23. Synthesis and Antileukemic Activity of Camptothecin Analogues", pp. 2358–2363.

J. Med. Chem., vol. 29, 1986, Monroe E. Wall, et al., "Plant Antitumor Agents. 22. Isolation of 11–Hydroxycamptothecin from Camptotheca Acuminata Decne: Total Synthesis and Biological Activity", pp. 1553–1555.

J. Med. Chem., vol. 23, 1980, Mansukh C. Wani, et al., "Plant Antitumor Agents. 18. Synthesis and Biological Activity of Camptothecin Analogues", pp. 554–560.

Cancer Treatment Reports, vol. 71, No. 4, Apr. 1987, Hiroshi Nagata, et al., "Action of 7–Ethylcamptothecin on Tumor Cells and Its Disposition in Mice", pp. 341–348.

Cancer Research, vol. 49, Aug. 15, 1989, Yaw–Huei Hsiang, et al., "DNA Topoisomerase I–Mediated DNA Cleavage and Cytotoxicity of Camptothecin Analogues", pp. 4385–4389.

Cancer Research, vol. 49, Mar. 15, 1989, Christine Jaxel, et al., "Structure–Activity Study of the Actions of Camptothecin Derivatives on Mammalian Topoisomerase I: Evidence for a Specific Receptor Site and a Relation to Antitumor Activity", pp. 1465–1469.

Science, vol. 246, Nov. 24, 1989, Beppino C. Giovanella, et al., "DNA Topoisomerase I–Targeted Chemotherapy of Human Colon Cancer in Xenografts", pp. 1046–1048.

Proceedings of the Annual Meeting of the American Association for Cancer Research, 1988, AN 29:A1080, Y. Pommier, et al., "Structure–Activity Study of the Relation Between Topoisomerase I Inhibition and Antitumor Activity of Camptothecin" (Abstract).

INHIBITION OF PLASMODIA PARASITES BY CAMPTOTHECIN COMPOUNDS

The United States government may have rights in this application.

BACKGROUND OF THE INVENTION

1. Field of the Invention

This invention relates to the inhibition of parasitic protozoa of the genus Plasmodium with camptothecin compounds. Camptothecin compounds have the general ring structure shown below.

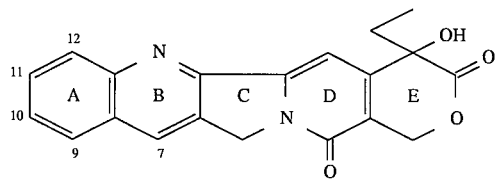

The invention also relates to the treatment of animals having plasmodia infections with camptothecin compounds.

2. Background of the Invention

Sporozoan protozoa of the genus Plasmodium are vertebrate parasites that infect primarily liver and red blood cells and may give rise to malaria. There are at least four species of plasmodia that normally infect humans, i.e., *P. vivax, P. ovale, P. malariae* and *P. falciparum*. Three additional species *P. cynomolgi, P. knowlesi* and *P. brasilianum* infect non-human primates.

Plasmodia infection is initiated by the bite of an infected insect, generally the female Anopheles mosquito, which injects infective sporozoites into the mammalian host. In the first stage of development, parenchyma cells of the liver are infected within which develop infective merozoites. Rupture of infected liver cells releases the merozoites into the blood stream where they infect circulating erythrocytes (red blood cells).

The parasites in the red blood cells multiply by ethrocytic schizogony dividing into erythrocytic merozoites. The host cell ruptures and merozoites are released into the bloodstream. The released parasites invade new red blood cells producing the symptoms of clinical malaria.

The periodic symptoms of malaria are related to the blood stream life cycle events of the plasmodia organisms. An initial chill begins as a generation of parasites rupture their host red cells and enter the blood stream. Nausea, vomiting and headache accompany this phase. A febrile stage follows the chill and is characterized by a spiking fever. During the febrile stage, parasites presumably enter new red blood cells. A sweating stage follows as the fever subsides.

Current therapy for plasmodia infection is treatment with one or more of the compounds quinine, chloroquine, amodiaquin, quinocide, primaquine, quinacrine, chloroguanide, pyrimethamine, trimethoprim, mefloquine, artemisinin, doxycycline, sulfadoxine and halofantrine. The large scale use of these drugs has resulted in the emergence of drug-resistant strains of plasmodia. During the 1960's, large scale use of chloroquine resulted in the emergence of chloroquine-resistance strains, for example. For chloroquine-resistant plasmodia infections, combinations of drugs are administered, for example a combination of pyrimethamine with sulfadoxin or quinine with sulphametopyrazine.

In view of the emergence of resistant plasmodia strains to existing drugs, a need continues to exist for new drugs that are toxic to plasmodia and/or suppress plasmodia infections.

SUMMARY OF THE INVENTION

Accordingly, one object of the present invention is to provide compounds that are cytotoxic to and can be used to inhibit the growth of organisms of the genus Plasmodium.

A further object is to provide compounds that are useful in treating plasmodia infections in livestock, domestic animals and humans.

These and other objects, which will become apparent from the following specification, have been achieved by the discovery that camptothecin and derivatives thereof are cytotoxic to plasmodia and are useful in treating plasmodia infections in animals and humans.

DETAILED DESCRIPTION OF THE PREFERRED EMBODIMENTS

In general, the present invention is directed to a method of inhibiting the growth of plasmodia organisms in an in vitro sample or in vivo in a mammal. Plasmodia which are inhibited by the compounds of the present invention are sporozoan protozoa of the genus Plasmodium. Specific plasmodia which are inhibited are *P. vivax, P. ovale, P. malariae, P. falciparum, P. knowlesi, P. cynomolgi* and *P. brasilianum*. The method of the present invention is particularly effective in inhibiting the growth of *P. falciparum* plasmodia.

An important aspect of this invention is the discovery that the anti-plasmodia activity of the camptothecin compounds of the present invention correlates closely with the activity of these compounds as inhibitors of the enzyme topoisomerase I. It has been discovered that camptothecin compounds, which actively inhibit the enzyme topoisomerase I in conventional in vitro tests, are effective inhibitors of plasmodia.

Any pharmaceutically or veterinarinally acceptable camptothecin compound or salt thereof exhibiting topoisomerase I inhibiting activity may be used in the present invention. By "exhibiting topoisomerase I inhibiting activity" is meant a camptothecin compound which exhibits an $IC_{50}$ value for topoisomerase I inhibition by the clearable complex assay of Hsiang et al. of 1.0 µM or less. The ability of camptothecin compounds to inhibit the enzyme topoisomerase I can be readily evaluated using the cleavable complex assay described in U.S. Pat. No. 5,244,903 and Hsiang et al., (1985), *J. Biol Chem.*, 260:14875–14878. Particularly preferred compounds are camptothecin derivatives having the (S) configuration at the 20-position and exhibiting topoisomerase I inhibitory activity equal to or greater than the activity of 20(S)-camptothecin (referred to below as 20(S)-CPT).

Camptothecin compounds and salts thereof which are known to exhibit topoisomerase I inhibitory activity are described, for example, in U.S. Pat. Nos. 4,894,456, 4,981,968, 5,053,512, 5,049,668, 5,106,742, 5,180,722, 5,244,903, 5,227,380, 5,122,606, 5,122,526, 5,225,404, 4,914,205, 4,545,880, 4,604,463, 4,473,692, 4,031,098, EP 0 220 601, EP 0 074 256 and U.S. patent application Ser. Nos. 07/784,275 and 07/826,729 (EP 0 540 099). These U.S. Applications and U.S. Patents are incorporated herein by reference for a more complete description of camptothecin compounds which can be used in the present invention.

Camptothecin and derivatives thereof have an asymmetric carbon atom at the 20-position and therefore exist in two enantiomeric forms, i.e. the (R) and (S) configurations. This invention includes both enantiomeric forms and all combinations of these forms, including racemic mixtures designated as (RS).

Preferred camptothecin compounds for use in the method of the present invention are 20(S)-CPT and derivatives thereof in which the A ring is unsubstituted or there is a substituent at the 9-, 10- or 9- and 10,11-positions. Suitable compounds have the structure shown below.

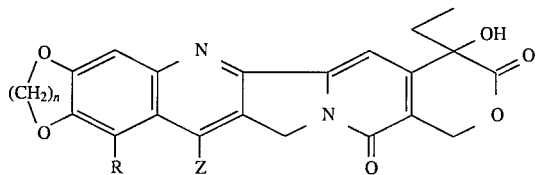

In the structure shown above, R is $NO_2$, $NH_2$, $N_3$, hydrogen, halogen (F, Cl, Br, I), COOH, OH, O—$C_{1-3}$ alkyl, SH, S—$C_{1-3}$ alkyl, CN, $CH_2NH_2$, NH—$C_1$·alkyl, $CH_2$—NH—$C_{1-3}$ alkyl, $N(C_{1-3}$ alkyl$)_2$, $CH_2N(C_{1-3}$ alkyl$)_2$, O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2CH_2OH)_2$, O—, NH— and S—$CH_2CH_2N(CH_2CH_2CH_2OH_2)_2$, O—, NH— and S—$CH_2CH_2N(C_{1-3}$ alkyl$)_2$, O—, NH— and S—$CH_2CH_2CH_2N(C_{1-3}$ alkyl$)_2$, CHO or $C_{1-3}$ alkyl. Preferred compounds are those in which R is halogen, nitro or amino.

Z in the structure shown above is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (b) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy- $C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups. In the structure shown above, n is an integer of 1 or 2.

Preferred aryl groups are phenyl and naphthyl. Also preferred are compounds having the structure shown above where Z is methyl, ethyl or propyl.

Preferred camptothecin compounds which are preferably substituted in the 9- or 10- position and can be used in the present invention have the structure shown below.

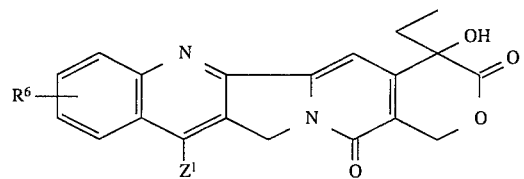

In this structure, $R^6$ is hydrogen, cyano, formyl, hydroxy, $C_{1-8}$ alkoxy, nitro, amino, halogen (I, Br, Cl, F), $C_{1-8}$ alkyl, trifluoromethyl, aminomethyl, azido, amido, hydrazino, $OC(O)R^7$ or OC(O)—$NR^7R^8$, where $R^7$ and $R^8$ are, independently, hydrogen or $C_{1-8}$ alkyl and $Z^1$ has the same definition as Z described above, preferably methyl, ethyl or propyl.

The lactone ring of the camptothecin compounds shown above may be opened by alkali metal or alkaline earth metal bases, for example, sodium hydroxide or calcium hydroxide to form alkali metal or alkaline earth metal salts of the open ring form of the camptothecin compounds. Open ring compounds have better solubility in water.

The preparation of these preferred compounds is described in U.S. Pat. Nos. 4,894,456, 5,180,722 and EP 0 540,099.

Additional camptothecin compounds which may be used in the present invention are camptothecin compounds in which the hydroxyl group at the 20-position has been esterified with the alpha-carboxyl group of a naturally occurring amino acid to form a group of the formula —OC(O)—$(CH_2)_m$—$NR^{10}R^{11}$, where m=1–6 or —$OC(O)CHR^9NR^{10}R^{11}$, where $R^9$ is the side chain of one of the naturally occurring α-amino acids, $R^{10}$ and $R^{11}$ are, independently, hydrogen or $C_{1-8}$ alkyl. Suitable side chains $R^9$ are the side chains of the amino acids glycine, alanine, valine, leucine, isoleucine, phenylalanine, tyrosine, tryptophan, lysine, arginine, histidine, aspartate, glutamate, asparagine, glutamine, cysteine and methionine. Particularly preferred esters are glycinate esters. These esters are prodrugs which are converted to the camptothecin compound by hydrolysis of the ester bond. The esters may be prepared by the method described in U.S. Pat. No. 4,943,579 which is incorporated herein by reference for a more complete description of the process of preparing the esters and for a description of suitable esters formed by the process.

Particularly preferred camptothecin compounds are selected from the group consisting of 7-methyl-10,11-methylenedioxy-20(S)-camptothecin, 7-ethyl-10,11-methylenedioxy-20(S)-camptothecin, 7-ethyl-9-amino-10,11-methylenedioxy-20(S)-camptothecin, 7-ethyl-9-nitro-10,11-methylenedioxy-20(S)-camptothecin, 7-ethyl-10-nitro-20(S)-camptothecin, 7-ethyl-10-amino-20(S)-camptothecin, 7-ethyl-20(S)-camptothecin, 7-propyl-20(S)-camptothecin, 7-ethyl-9-amino-20(S)-camptothecin, 7-ethyl-9-nitro-20(S)-camptothecin, 9-amino-10,11-methylenedioxy-20(S)-camptothecin, 9-chloro-10,11-methylenedioxy-20(S)-camptothecin, 10,11-methylenedioxy-20(S)-camptothecin, 9-chloro-20(S)-camptothecin, 10,11-methylenedioxy-20-glycinate-20(S)-camptothecin, 9-amino-20(S)-camptothecin, 10-amino-20(S)-camptothecin, 10-chloro-20(S)-camptothecin and 20(S)-camptothecin.

The method of the present invention, i.e., inhibiting the growth of plasmodia organisms by contacting the organisms with a camptothecin compound which inhibits the enzyme topoisomerase I, is useful as a control in screening assays in which plasmodia strains are assayed for their sensitivity to known anti-plasmodia chemotherapeutic drugs such as chloroquine. In these assays, the drug-resistance of a particular plasmodia strain can be determined by growing the plasmodia strain in the presence of specific anti-plasmodia compounds as positive controls. For example, when a plasmodia strain is discovered which is resistant to chloroquine, the strain should be assayed for its resistance to a battery (plurality) of known anti-plasmodia drugs including one or a plurality of the camptothecin compounds of the present invention. The assay provides a means of determining which single camptothecin compound or which combination of camptothecin compounds or combination of a camptothecin compound and conventional anti-plasmodia compound are best suited to inhibit growth of the plasmodia strain. Typically, the assay will use the positive control compounds at a variety of concentrations to determine the $IC_{50}$ value for the specific compound against the plasmodia strain. The assay procedure and the specific concentrations of positive control compounds can be readily determined by one having ordinary skill in this art. Table 1 below provides an example of this type of assay using two drug resistant plasmodia clones.

The camptothecin compounds are administered in a dose which is effective to inhibit the erythrocytic schizogony of the plasmodia. As used herein, an effective amount of the plasmodia inhibiting camptothecin compounds is intended to mean an amount of the compound that will inhibit the growth of growing plasmodia, that is, reduce the number of growing plasmodia relative to a control in which the plasmodia are not treated with the camptothecin compound. These effective amounts are generally from about 1–60 mg/kg of body weight per week, preferably about 2–20 mg/kg per week.

The compounds of the present invention may be administered as a pharmaceutical or veterinary composition containing the camptothecin compound and a pharmaceutically or veterinarially acceptable carrier or diluent. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically or veterinarially pure and non-toxic in the amounts used.

The compounds of the present invention may also be administered in the form of liposome or microvesicle preparations. Liposomes are microvesicles which encapsulate a liquid within lipid or polymeric membranes. Liposomes and methods of preparing liposomes are known and are described, for example, in U.S. Pat. Nos. 4,452,747, 4,448,765, 4,837,028, 4,721,612, 4,594,241, 4,302,459 and U.S. Pat. No. 4,186,183. The disclosures of these U.S. patents are incorporated herein by reference. The compounds of the present invention may be formulated according to these methods and administered in liposome microvesicles.

The camptothecin compounds may be used individually to inhibit the growth of plasmodia organisms. Alternatively, combinations of two or more camptothecin compounds may be used or combinations of one or more camptothecin compounds with one or more known anti-plasmodia compounds such as quinine, chloroquine, pyrimethamine, mefloquine, etc. When a camptothecin compound is combined with a conventional anti-plasmodia compound, the camptothecin compound will generally be present in an amount ranging from about 1–99 wt. %, preferably, 5–95 wt. % of the combined amount of camptothecin and conventional anti-plasmodia compound. The pharmaceutical and veterinary compositions noted above may contain these combinations of compounds together with an acceptable carrier or diluent.

In addition to treatment of humans, the camptothecin compounds of the present invention may be used to inhibit growth of plasmodia in livestock animals such as cows, horses, pigs, sheep and goats as well as in domesticated animals such cats and dogs.

A further important aspect of the present invention is the overall low toxicity of the camptothecin compounds when administered as described herein. The low toxicity of camptothecin compounds when administered for antitumor therapy is described, for example, in U.S. Pat. No. 5,225,404.

Other features of the invention will become apparent in the course of the following descriptions of exemplary embodiments which are given for illustration of the invention and are not intended to be limiting thereof.

EXAMPLES

The activity of camptothecin compounds to inhibit plasmodia growth was tested in two different systems. All compounds were tested for their ability to inhibit the growth of a *P. falciparum* strain (W2; CDC/Indochina III) which is resistant to chloroquine, quinine and pyrimethamine, but sensitive to mefloquine, artemisinin and halofantrine, and a P. falciparum strain (D6; Oduola et al., 1988, Exp. Parasitol., 66(1):86–95), which is sensitive to chloroquine, quinine, pyrimethamine, artemisinin and halofantrine, but resistant to mefloquine.

These strains (clones) were maintained in continuous log-phase growth in RPMI-1640 medium supplemented with 6% washed human A+ erythrocytes, 25 mM HEPES, 32 nM $NaHCO_3$, and 10% heat inactivated A+ human plasma or ALBUMAX (lipid-rich bovine serum albumin, GIBCO, Grand Island, N.Y.). All cultures and assays were conducted at 37° C. under an atmosphere of 5% $CO_2$ and 5% $O_2$, with a balance of $N_2$.

The screening tests assess the intrinsic activity of the tested compounds against the erythrocytic asexual lifecycle (blood schizontocides). The screening test is based on modifications of known procedures (Chulay et al., 1983, Exp. Parasitol, 55:138–146; Desjardins et al., 1979, Antimicrob. Agents Chemother., 16:710–718; Milhouse et al., 1985, Antimicrob. Agents Chemother., 27:525–530).

A preliminary screen used D6 diluted to a 0.2% parasitemia in a 1% hematocrit in folic acid free and p-aminobenzoic acid free RPMI-1640 (GIBCO, Grand Island, N.Y.) and ALBUMAX (FF-CM). Five mg of the camptothecin compound where dissolved in 250 µl of dimethyl sulfoxide (DMSO). The compound was further diluted to a stock solution to 10 ml with FF-CM. This stock solution was kept at −70° C. until used. The strain was preexposed, in duplicate, at three concentrations (50,000 ng/ml, 5,000 ng/ml, and 50 ng/ml) of the test compound for 48 hr in a 96-well microtiter plate (MTP) using the BIOMEK 1000 automated laboratory workstation (Beckman Instruments, Fullerton, Calif.). Each MTP contained chloroquine-containing controls to assess the relative activity of the unknown compound and to monitor the response of D6.

After the preincubation, $^3$H-hypoxanthine was added to each well of the MTP to determine if the parasites could still replicate or repair DNA. After 66 hr of total incubation time, the MTP were frozen to lyse the erythrocytes and parasites. The parasite DNA was recovered by harvesting the lysate onto glass-fiber filters using a Mark II cell-harvester (Torntec, Orange, Conn.). The radioactivity was counted on a 1205 BETAPLATE liquid scintillation counter (Wallac, Turku, Finland). The results were recorded as counts per minute (CPM) per well at each drug concentration divided by the arithmetic mean of the CPM from the three untreated infection parasite controls wells.

If the compound did not affect parasite growth at 50,000 ng/ml, it was classified as inactive. If the compound suppressed greater than two standard deviations from the arithmetic mean of the untreated infection controls at 50,000 ng/ml, but less than 50% at 5,000 ng/ml, the compound was designated as partially active. However, if the compound suppressed greater than 50 percent of the incorporation of $^3$H-hypoxanthine relative to untreated infection control parasites at 5,000 ng/ml, the compound was classified as active and was further evaluated by two-fold serial dilutions to determine the $IC_{50}$ values (50% inhibitory concentration) for each compound.

The serial dilution assay was conducted using the same assay conditions and stock solution of the compound used for the preliminary screen. Both the D6 and the W2 strains were used. The compound was diluted two-fold over 11 different concentration ranges with a starting concentration that was based on the preliminary screen. The $IC_{50}$ was determined by a non-linear logistic dose response analysis (TABLECURVE, Jandel Scientific, Corte Madera, Calif.). If the results from this assay did not agree with the concentration ranges of the preliminary screen, the assay was repeated. For each assay, the $IC_{50}$ for each strain was determined against the known antimalarials chloroquine, mefloquine, artemisinin, quinine, and pyrimethamine. These control values establish the camptothecin compound's relative parasite susceptibility profile compared to known antimalarials. $IC_{50}$s can be similarly determined for drug-resistant isolates/clones from a wide variety of geographic locations.

The results of the tests on drug resistant P. falciparum are shown in Table 1 below.

TABLE 1

| | Inhibition of P. falciparum | |
|---|---|---|
| Compound | W2[1] | D6[1] |
| 20(S)-CPT[2] | 283 | 254 |
| 10-amino-20(S)-CPT | 72.4 | 56.8 |
| 9-amino-20(S)-CPT | 149 | 116 |
| 10-chloro-20(S)-CPT | 673 | 823 |
| 9-chloro-20(S)-CPT | 643 | 584 |
| 7-ethyl-20(S)-CPT | 63.2 | 55.0 |
| 7-n-propyl-20(S)-CPT | 100 | 92.8 |
| 10,11-MD-20(S)-CPT[3] | 2.43 | 1.49 |
| 9-amino-10,11-MD-20(S)-CPT | 5.11 | 4.42 |
| 9-chloro-10,11-MD-20(S)-CPT | 8.72 | 8.14 |
| 7-methyl-10,11-MD-20(S)-CPT | 7.23 | 8.83 |
| 7-ethyl-10,11-MD-20(S)-CPT | 6.59 | 6.10 |
| 10,11-MD-20(S)-glycinate ester-CPT-HCl | 40.2 | 31.9 |

[1]Values are reported as $IC_{50}$ values in ng/ml
[2]CPT = camptothecin
[3]MD = methylenedioxy Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of inhibiting plasmodia growth, comprising contacting living plasmodia with an effective inhibitory amount of a camptothecin compound which has the structure shown below

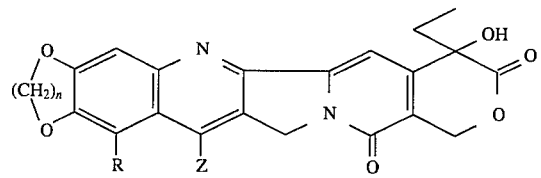

wherein in the structure shown above, R is $NO_2$, $NH_2$, $N_3$, hydrogen, halogen, COOH, OH, O—$C_{1-3}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2$N($C_{1-3}$ alkyl)$_2$, O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2CH_2OH)_2$, O—, NH— and S—$CH_2CH_2CH_2N(CH_2CH_2CH_2OH_2)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl;

Z in the structure shown above is H, $C_{1-8}$ alkyl, or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl, (b) $R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy- $C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR^5$ where $R^5$ is hydrogen, $C_{1-6}$ alkyl perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$ alkyl, or $C_{1-6}$ alkoxy-$C_{1-6}$ alkyl groups;

n is an integer of 1 or 2; and pharmaceutically or veterinarially acceptable salts thereof wherein said compound exhibits topoisomerase I inhibitory activity.

2. The method of claim 1, wherein said camptothecin compound exhibits an $IC_{50}$ value of 1.0 μM or less in a cleavable complex assay for topoisomerase I inhibitory activity.

3. The method of claim 1, wherein the OH group at the 20-position of said camptothecin compound is esterified to form a group of the formula —$OC(O)CHR^9NR^{10}R^{11}$, where $R^9$ is the side chain of a naturally occurring α-amino acid and $R^{10}$ and $R^{11}$ are, independently, hydrogen or $C_{1-8}$ alkyl.

4. The method of claim 1, wherein said camptothecin compound is selected from the group consisting of 7-methyl-10,11-methylenedioxy-20(S)-camptothecin, 7-ethyl-10,11-methylenedioxy-20(S)-camptothecin, 7-ethyl-9-amino-10,11-methylenedioxy-20(S)-camptothecin, 7-ethyl-9-nitro-10,11-methylenedioxy-20(S)-camptothecin, [7-ethyl-10-nitro-20(S)-camptothecin, 7-ethyl-10-amino-20(S)-camptothecin, 7-ethyl-20(S)-camptothecin, 7-propyl-20(S)-camptothecin, 7-ethyl-9-amino-20(S)-camptothecin, 7-ethyl-9-nitro-20(S)-camptothecin,] 9-amino-10,11-methylenedioxy-20(S)-camptothecin, 9-chloro-10,11-methylenedioxy-20(S)-camptothecin, 10,11-methylenedioxy-20(S)-camptothecin, and [9-chloro-20(S)-camptothecin,] 10,11-methylenedioxy-20-glycinate-20(S)-camptothecin[,9-amino-20(S)-camptothecin, 10-amino-20(S)-camptothecin, 10-chloro-20(S)-camptothecin and 20(S)-camptothecin].

5. The method of claim 4, wherein the OH group at the 20-position of said camptothecin compound is esterified to form a group of the formula —$OC(O)CHR^9NR^{10}R^{11}$, where $R^9$ is the side chain of a naturally occurring α-amino acid and $R^{10}$ and $R^{11}$ are independently, hydrogen or $C_{1-8}$ alkyl.

6. The method of claim 1, wherein said plasmodia is a Plasmodium organism selected from the group consisting of *P. vivax, P. ovale, P. malariae, P. falciparum, P. knowlesi, P. cynomolgi* and *P. brasilianum*.

7. The method of claim 6, wherein said organism is *P. falciparum*.

8. The method of claim 1, wherein said contacting comprises administering said camptothecin compound to a mammal.

9. The method of claim 8, wherein said effective inhibitory amount comprises 1–60 mg/kg of body weight per week.

10. The method of claim 9, wherein said effective inhibitory amount comprises about 2–20 mg/kg of body weight per week.

11. The method of claim 9, comprising parenterally administering said camptothecin compound to said mammal.

12. The method of claim 9, comprising orally administering said camptothecin compound to said mammal.

13. The method of claim 9, wherein said mammal is selected from a group consisting of cows, horses, pigs, sheep, goats, cats, and dogs.

14. The method of claim 9, wherein said mammal is a human.

* * * * *